United States Patent
Houssais

(10) Patent No.: US 8,616,076 B2
(45) Date of Patent: Dec. 31, 2013

(54) TEST DEVICE FOR TESTING FLEXIBLE SEPARATORS

(75) Inventor: Alain Houssais, L'Isle-Adam (FR)

(73) Assignee: Olaer Industries, Colombes (FR)

( * ) Notice: Subject to any disclaimer, the term of this patent is extended or adjusted under 35 U.S.C. 154(b) by 426 days.

(21) Appl. No.: 12/957,889

(22) Filed: Dec. 1, 2010

(65) Prior Publication Data

US 2011/0132072 A1 Jun. 9, 2011

(30) Foreign Application Priority Data

Dec. 4, 2009 (FR) ..................................... 09 58672

(51) Int. Cl.
*G01N 19/00* (2006.01)
(52) U.S. Cl.
USPC ...... 73/865.9; 73/864; 73/864.15; 73/864.16; 73/864.17
(58) Field of Classification Search
USPC ......... 73/865.9, 864, 863.16, 864.17, 864.16, 73/864.51
See application file for complete search history.

(56) References Cited

U.S. PATENT DOCUMENTS

| 5,280,874 A * | 1/1994 | Zink et al. ..................... 251/144 |
| 2005/0163721 A1* | 7/2005 | Harman ........................... 424/45 |

FOREIGN PATENT DOCUMENTS

GB 1 389 680 4/1975

* cited by examiner

*Primary Examiner* — Hezron E Williams
*Assistant Examiner* — Rodney T Frank
(74) *Attorney, Agent, or Firm* — Hamre, Schumann, Mueller & Larson, P.C.

(57) ABSTRACT

Testing the reliability of flexible separators arranged under conditions enabling the cycling rate of testing to be accelerated. According to the invention, two separators are enclosed in two rigid chambers, each defining a liquid capacity and a gas capacity. The two gas capacities communicate with each other, and each of the liquid capacities communicates with means for causing the volume of each of them to vary in alternation.

17 Claims, 3 Drawing Sheets

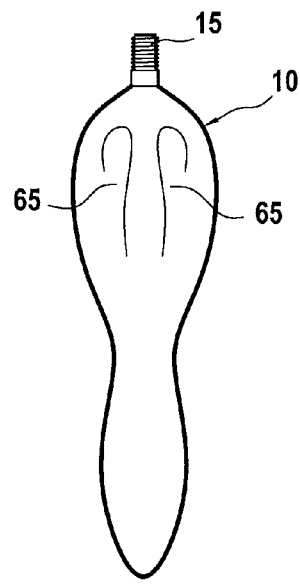
FIG.2
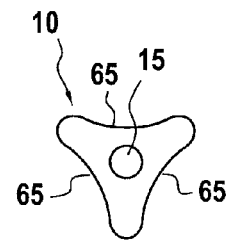
FIG.3
FIG.5
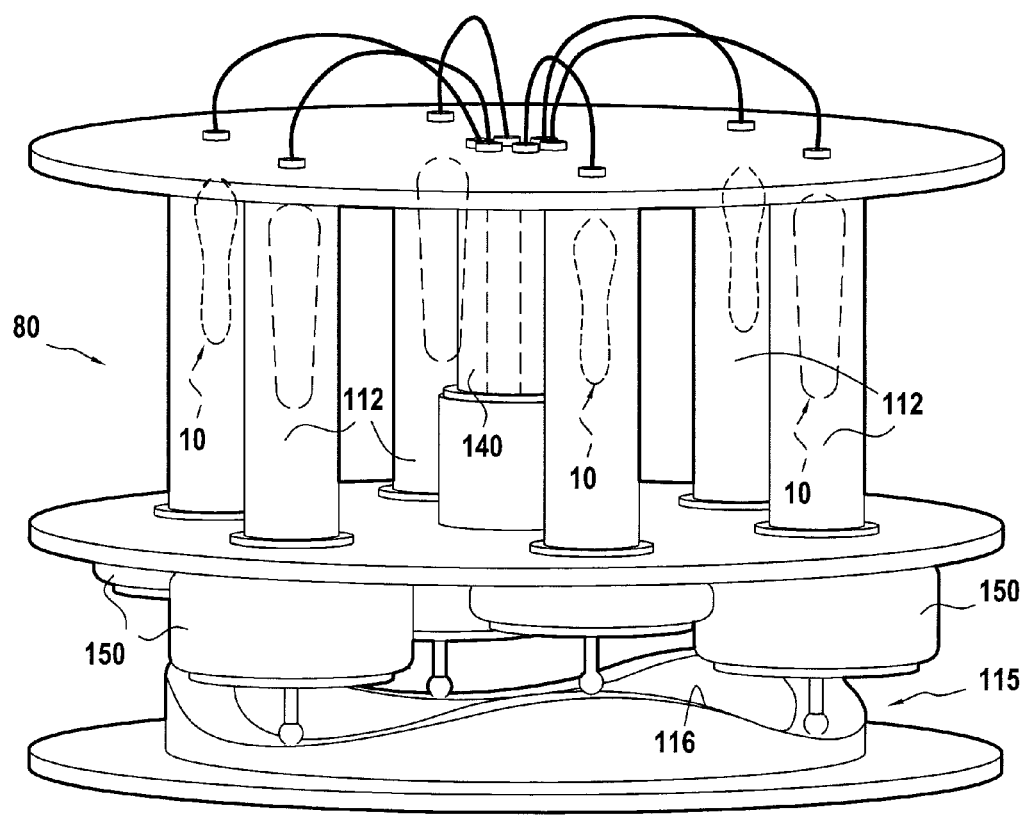

TEST DEVICE FOR TESTING FLEXIBLE SEPARATORS

FIELD OF THE INVENTION

The invention relates to a method and a device for testing the reliability of a flexible separator associated with a rigid chamber and subdividing the chamber into a liquid capacity and a gas capacity of volumes that are variable, such as in particular the flexible separators that separate a liquid and a gas in so-called "hydraulic" accumulators.

The variations in the respective volumes of the liquid and gas capacities give rise to repetitive deformation of the flexible separator and thus, after a certain length of time, to rupture of the flexible separator. The reliability of a flexible separator thus determines the reliability of the apparatus in which it is associated.

BACKGROUND OF THE INVENTION

In order to evaluate the reliability, e.g. of a hydraulic accumulator, it is known to mount such an accumulator fitted with a flexible separator on a test bench that includes means for causing the volume of liquid to vary cyclically, thereby deforming the flexible separator. That method of testing the reliability of a separator requires the test bench to be fitted with a hydraulic circuit that is complex and relatively vulnerable, in particular because of the need to provide means such as, for example: a four-port valve for reversing the flow direction of liquid through the accumulator, so as to vary the volume and the deformation of the separator. Furthermore, the inertia and the head losses inherent to such a hydraulic circuit limit the rate at which deformation cycles can alternate. The duration of reliability tests for a large number of cycles is therefore very long. That is why, for industrial and economic reasons, one is often encouraged to limit the number of cycles. That raises problems in certain applications where reliability needs to be very high and where it is desirable to continue testing beyond 10,000,000 cycles, i.e. all the way to rupture even though testing is often presently limited to no more than 2,000,000 cycles, for the reasons mentioned above.

OBJECT AND SUMMARY OF THE INVENTION

The method of the invention is designed, amongst other things, to avoid the need for a complex hydraulic circuit and to make it possible to accelerate the rate of cycling (4 hertz (Hz) to 6 Hz, instead of 1 Hz or 2 Hz), thereby significantly shortening the duration of testing while continuing testing until rupture of a separator. Furthermore, because of its "push-pull" mode of operation, the method of the invention gives rise to energy consumption that is well below that of the prior art system, as recalled above, and does so with a structure that is relatively simple and inexpensive.

Furthermore, the method makes use of a pressure that is well below the utilization pressure of the separator in service. In this respect, it should be recalled that certain hydraulic accumulators that use a flexible separator, e.g. an elastomer bladder, are designed so that utilization pressures may exceed 700 bar, whereas the device of the invention can operate at a pressure of the order of 2 bar to 3 bar.

The fact of using pressure that is low but substantially in the same liquid/gas compression ratio, gives rise to comparable amounts of separator deformation while allowing deformation cycles to be performed at a high rate (a few hertz), thereby enabling the lifetime of the separator as such to be better evaluated by running tests until separator rupture in lengths of time that are shorter and acceptable, given industrial constraints. The invention enables this object to be achieved.

Most particularly, the invention provides a test device for testing a flexible separator, said separator being of the type designed to constitute the bladder in a hydraulic accumulator, wherein the device comprises at least two similar rigid chambers each receiving an above-mentioned separator mounted in leaktight manner to define a liquid capacity between the rigid chamber and the outside wall of the separator, and a gas capacity constituted by the inside of the separator itself, wherein the two gas capacities are in permanent communication throughout the test, and wherein the two liquid capacities communicate with respective means for causing the volume of liquid in each of them to vary by the same amount in alternation and in phase opposition.

The variations in liquid volume in each of the two liquid capacities are substantially equal.

The test takes place on two similar separators of the above-specified type. In a destructive test, cycles are counted until one of the separators ruptures.

The arrangement as defined above provides good and repetitive control over the deformation of the separator by controlling the transfers of liquid and gaseous fluid both outside and inside the bladder-forming separator. It is thus ensured, from one cycle to another, that the separator always deforms in the same manner and always under conditions that correspond to normal utilization conditions. Using two similar separators in push-pull makes it a simple manner to obtain good control over the deformation thereof, however it should be observed that any installation, even if more complex, should be considered as being in accordance with the invention, providing it is suitable for repetitively controlling transfers of gas and liquid from either side of such a separator so that its deformation is substantially identical from one cycle to another and so that its deformation corresponds to the deformation of the separator under normal conditions of use.

The interaction between the two gas capacities giving rise to a driving reaction force due to the flow of gas entering into one and then the other capacity in alternation, makes it possible, without having recourse to additional means that are complex, e.g. such as pneumatic regulation loops, to ensure that the deformation characteristics of the flexible separators are kept constant in the desired manner, such as being certain that the same number of cycles is actually performed by both bladders, throughout the running of the test.

In an embodiment, each liquid capacity communicates directly with a deformable chamber, and said deformable chambers have the same volume and are coupled to actuator means suitable for imparting similar deformations thereto in phase opposition.

For example, each deformable chamber is in the form of a deformable bag in communication with one end of the corresponding rigid chamber, and the bags are coupled to a lever having a fulcrum point that is equidistant between the axes of said bags.

Preferably, each bag carries a rigid bottom to which the lever is hinged.

In another possible variant, the two liquid capacities communicate with respective chambers of a two-rod actuator. Means are provided for moving the piston in alternation and with the same amplitude on either side of an intermediate position.

In a possible embodiment, one end of the lever is connected to a drive mechanism oscillating at an amplitude that is adjustable, e.g. comprising a disk that is driven by a motor and that is associated with a connecting rod that is hinged between the disk and the lever. Different potential hinge points are provided between the disk and the connecting rod so as to enable variations of amplitude to be adjusted and thus so as to enable variations of compression to be adjusted for the deformable capacities and consequently for the quantity of liquid that is moved on each cycle.

In a possible embodiment, the two gas capacities communicate with each other and with a common rigid intermediate capacity. The volume of this intermediate capacity is preferably determined so as to limit the heating of the system as a function of the frequency of the cycles.

In a possible embodiment, the rigid intermediate capacity includes a liquid detector. Thus, the detector serves to detect a leak of liquid resulting from rupture of a separator. The detector is preferably operationally connected both to a system for stopping the device and to the associated cycle counter. In this way, it is possible to perform deformation cycles until rupture of the separator and to count the number of deformations to which the separator is subjected before it ruptures.

The above-described device is not limited to a pair of separators operating in push-pull. Such a test device may include a plurality of pairs of the above-described rigid chambers receiving the above-described separators, with the corresponding gas capacities of each pair communicating with each other.

For example, the rigid chambers may be arranged side by side around a circle and the above-mentioned means for causing the volume of liquid in the liquid capacities of each pair to vary in alternation and in phase opposition may comprise a common actuator mechanism comprising a cam-forming ring (e.g. a sinusoidal cam), said cam being driven in rotation about an axis passing through the center of the circle around which said rigid chambers are arranged.

BRIEF DESCRIPTION OF THE DRAWINGS

The invention can be better understood and other advantages thereof appear more clearly in the light of the following description of embodiments of a device enabling the endurance of a flexible membrane separator to be tested, given purely by way of example and made with reference to the accompanying drawings, in which:

FIG. 2 is a detail view showing the shape of the separator when it is deformed under the action of the liquid;

FIG. 3 is a plan view of the FIG. 2 separator;

FIG. 5 is a general diagrammatic view in perspective of another embodiment of a device in accordance with the invention.

MORE DETAILED DESCRIPTION

Figure 1:
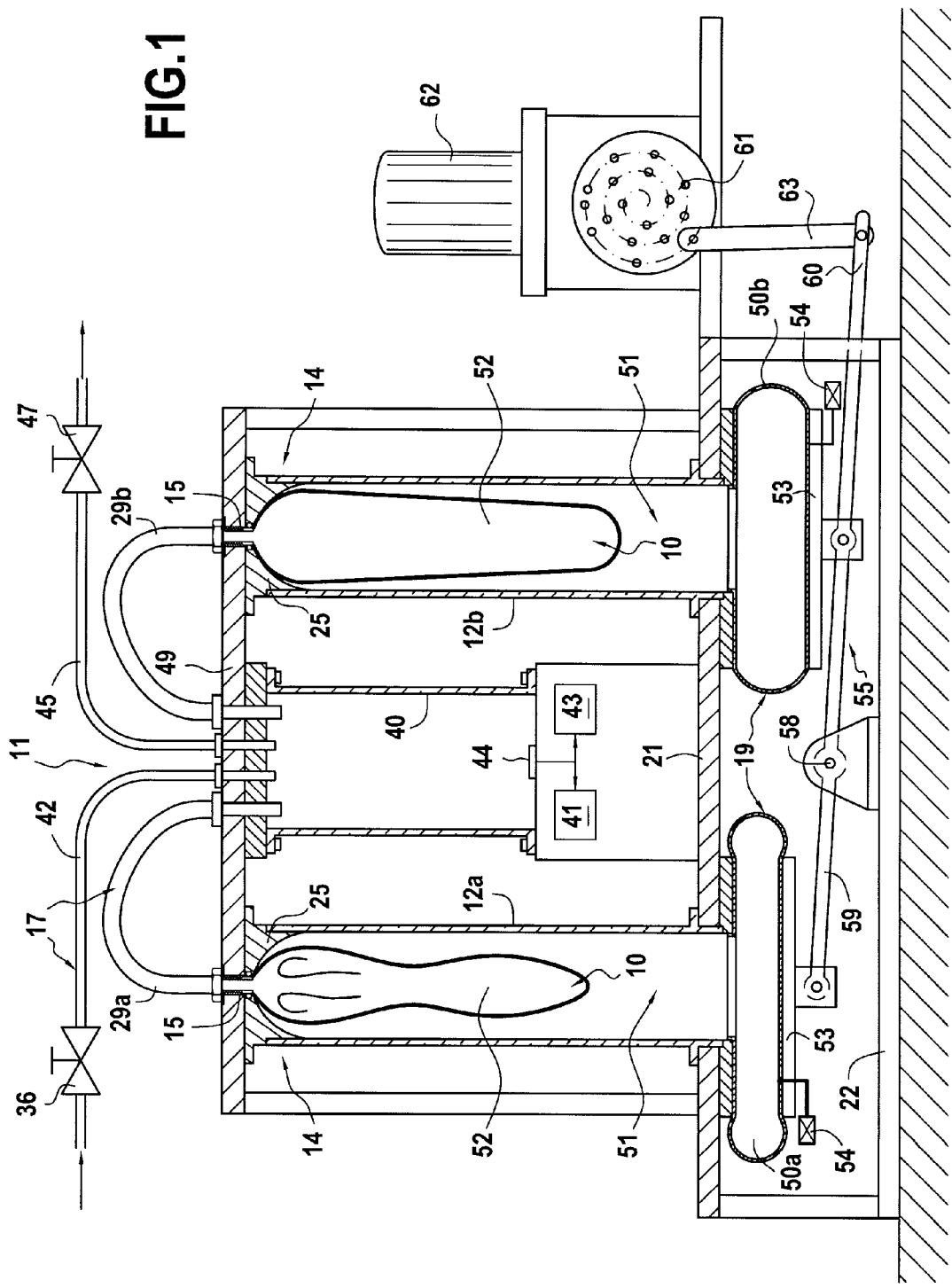
FIG. 1 is a diagrammatic elevation view of a test device of the invention.

The device 11 shown in FIGS. 1 to 3 receives two identical flexible separators 10 in the form of "bladders". In this example, it comprises two rigid chambers 12a, 12b that are generally cylindrical and tubular, each suitable for receiving one separator 10. At its top end, each chamber 12a, 12b includes a sealed connection arrangement 14 enabling a tubular endpiece 15 of the separator 10 to be fitted in leaktight manner to said top end. The device 11 may also have means 17 for enclosing a gas at a predetermined pressure within the separators (i.e. inside the "bladders") and means 19 for moving a liquid cyclically into and out of each rigid chamber 12a, 12b, i.e. on the outside of the separator engaged therein. This cyclical motion of the liquid has the consequence of causing the separators filled with gas under pressure to describe deformation cycles that makes it possible to evaluate their lifetime.

In the example, both rigid chambers 12a, 12b are fastened vertically on an intermediate plate 21 that is horizontal. The intermediate plate is itself mounted above a base 22 so as to constitute a hollow stand housing a portion of the means 19 for moving the liquid in alternation in the rigid chambers 12a, 12b.

Each rigid chamber 12a, 12b includes a cap 25 at its top end, the center of the cap being pierced to pass the tubular endpiece 15 of the separator. The endpiece is connected to a corresponding duct element 29a, 29b. The separator 10 is installed in the corresponding rigid chamber 12a, 12b in oil-tight manner so that the liquid engaged under pressure in said rigid chamber cannot escape around the endpiece 15. The assembly is leaktight, at least at the pressure of the endurance test (about 1 bar). This pressure is considerably less than the utilization pressure for which the separator is designed. This enables deformation cycles to be applied thereto at a high rate, i.e. a rate of several hertz.

The means 17 for containing gas under a predetermined pressure in the separators 10 comprise a source of nitrogen under pressure communicating with the separators via an isolation valve 36. This valve communicates via a corresponding duct element 29a, 29b with the tubular endpiece 15 of each separator.

In other words, said connection arrangement 14 of the two rigid chambers 12a, 12b are connected via a constant volume common connection so as to share the same quantity of gas under pressure, since both duct elements 29a, 29b communicate with the control valve 36. When the control valve 36 is open, a certain quantity of gas may be introduced into both separators 10. Thereafter, the control valve is closed so that a predetermined quantity of gas under pressure is shared between the two separators.

According to an advantageous characteristic, said common connection includes two duct elements 29a, 29b together with a rigid intermediate capacity 40 suitable for receiving a liquid. Each duct element 29a, 29b is connected to said intermediate capacity 40 and to said connection arrangement 14 of the corresponding rigid chamber 12a, 12b. The outlet from the valve 36 communicates via a duct 42 with the intermediate capacity 40. In addition, this capacity preferably includes a liquid detector 44 operationally connected to an alarm system 41 and/or to means for stopping a deformation cycle counter 43. When liquid (oil) penetrates into the intermediate capacity or container, that indicates that one of the separators 10 has failed, and it is appropriate to store the number of cycles that it withstood before rupturing.

A gas discharge duct 45 is connected to the intermediate capacity 40. It includes a discharge valve 47. During the test, this valve is closed.

The intermediate capacity 40 is advantageously transparent so that any presence of oil in this capacity or container, indicating that one of the separators has failed, can be detected both visually and electronically, by means of the signal provided by the detector 44.

A closure plate 49 serves to connect the duct elements 29a, 29b and the two ducts 42, 45 to said intermediate capacity. The top ends of the two chambers 12a, 12b together with their covers 25 are secured to said closure plate 49.

As mentioned above, a predetermined quantity of liquid is held captive around the flexible separators 10 and in said means 19 for moving the liquid cyclically. Advantageously, the liquid fills all of the above-defined available space.

Thus, for each separator 10, a liquid capacity 51 is defined between the outside wall of the separator and the rigid chamber, and a gas capacity 52 constituted by the inside of the separator itself. The two gas capacities 52 are permanently interconnected throughout the test and they also communicate with the intermediate capacity 40. Throughout the test, these interconnected elements thus contain a given quantity of gas under pressure and, throughout all of the exchanges between the separators, the total volume of gas held captive remains substantially constant.

In one possible embodiment, the means 19 for moving the liquid cyclically comprise two deformable chambers 50a, 50b communicating with respective ones of the rigid chambers 12a, 12b, together with an actuator mechanism 55 that is arranged so as to vary the volumes of the deformable chambers cyclically and in alternation. As can be seen in the drawings, each rigid chamber 12a, 12b is extended beyond its bottom end by a respective such deformable chamber 50a, 50b. These chambers are connected to a common actuator mechanism 55 arranged to make them operate in phase opposition.

In the example, the two deformable chambers 50a, 50b communicating respectively with the two rigid chambers 12a, 12b are actuated by means of a common lever 59 having a fulcrum point 58 that is equidistant between said deformable chambers. In the example, each deformable chamber 50a, 50b is in the form of a flexible bag in direct communication with the corresponding rigid chamber 12a, 12b. Each bag is connected to a plate 53 hinged to the lever 59. The plates 53 are hinged to the lever 59 on either side of and at equal distances from the fulcrum 58. One end 60 of the lever 59 is connected to a drive mechanism operating at adjustable amplitude and frequency and comprising a disk 61 driven by a motor 62 with a connecting rod 63 hinged between the disk and the lever. The disk 61 has a plurality of connection points for the connecting rod 63, which connection points are situated at different radial distances so as to enable the amplitude of the movement of the lever 59 to be adjusted. The variation in the quantity of liquid present in each chamber 12a, 12b is sinusoidal as a function of time. The liquid may be introduced into each bag via a stop valve 54 and a duct that passes through the plate 53. Naturally, other equivalent actuator mechanisms are possible.

Figure 4:
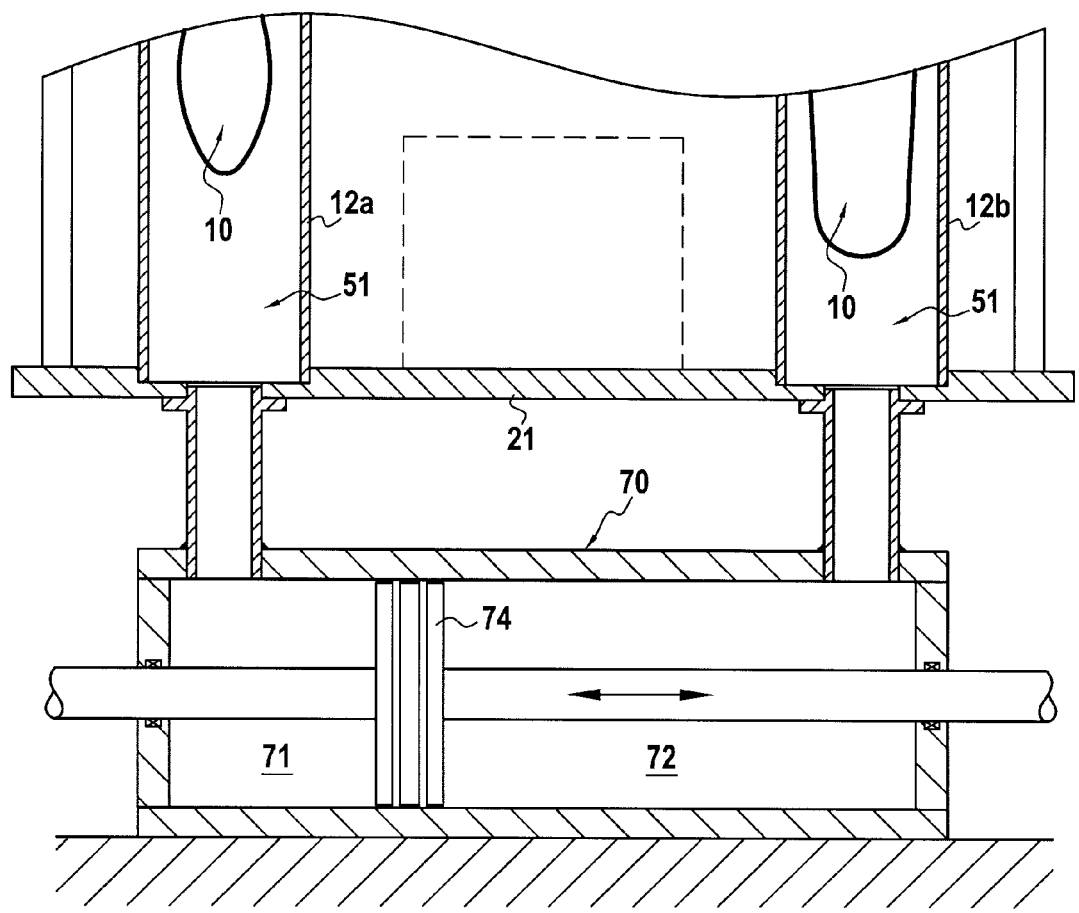
FIG. 4 is a diagrammatic view of a variant of the means for causing the volume of liquid in each of the liquid capacities of the FIG. 1 device to vary in alternation and in phase opposition.

For example, the bag and the lever could be replaced by an actuator 70 having two rods, as shown in FIG. 4.

The chambers 71 and 72 of the actuator are connected directly and respectively to the liquid capacities 51. The volumes of the chambers vary in phase opposition and by the same quantity when the piston 74 is moved in one direction and then in the opposite direction through the same amplitude.

Throughout the duration of the endurance test, each separator 10 is successively and cyclically compressed from the outside (thereby reducing its volume), and then relaxed so as to enable it to return to a normal volume. In FIG. 1, the separator being compressed on the outside is shown on the left, while the separator occupying its normal volume is shown on the right. Since the total of the volumes of oil moving respectively during each cycle remains substantially constant, and since both separators are permanently connected together by a common connection of constant volume (29a, 29b, 40), the pressure of the gas inside the two separators remains substantially constant. As shown in FIGS. 2 and 3, the separator 10 deforms in a specific manner by defining a plurality of longitudinal lobes 65 that create localized zones of fatigue. After a large number of cycles, the separator ends up by rupturing along one of these zones of fatigue. When rupture is detected, the number of cycles that have been performed is noted and serves to evaluate the lifetime of the separator in the form of a bladder.

FIG. 5 shows another possible device 80 that is remarkable in that it has a plurality of pairs of rigid chambers 112 of the above-described type that are arranged side by side around a circle. In this example, the device has three pairs of rigid capacities. These capacities are connected together pneumatically in the same manner as described with reference to FIG. 1, i.e. all of the separators 10 communicate in pairs and each pair is connected together so as to share a common quantity of gas under pressure.

In this embodiment, the means for moving the liquid cyclically in the capacities 112 are connected to a common actuator mechanism 115 comprising a ring forming a kind of sinusoidal cam 116. The cam is driven by a motor about an axis that passes through the center of the circle around which the rigid capacities 112 are arranged. More precisely, the sinusoidal cam co-operates with all of the deformable chambers 150 associated with said rigid chambers 112.

At the center of the equipment there is an intermediate capacity 140 that has three distinct compartments. Each compartment is put into communication with the gas capacities constituted by a pair of separators operated in phase opposition by the actuator mechanism 115.

What is claimed is:

1. A device for testing the reliability of flexible separators for separating a liquid fluid and a gaseous fluid, wherein the device comprises two identical rigid chambers, each of said chambers being subdivided by an identical flexible separator into a liquid capacity and a gas capacity, wherein the two gas capacities communicate with each other, and wherein the two liquid capacities communicate with means for causing the volume in each of the two liquid capacities to vary alternation, wherein the device further comprises a liquid detector to detect a leak of liquid resulting from the rupture of a separator.

2. A device according to claim 1, wherein the variations of liquid volume in each of the two liquid capacities are substantially identical.

3. A device according to claim 1, wherein each of the two liquid capacities communicates with a respective deformable capacity, the two deformable capacities having the same volume and being subjected in alternation to identical varying deformation.

4. A device according to claim 3, wherein the deformable capacities are in the form of bags, each of said bags being subjected via a plate-forming rigid bottom to the action of a lever oscillating about an axis that is equidistant between said bags and that exerts similar compression forces on said bags in alternation.

5. A device according to claim 4, wherein one end of said lever is connected to a drive mechanism presenting adjustable amplitude and frequency.

6. A device according to claim 5, wherein said mechanism comprises a motor driving a disk having connecting points at different radial distances, and wherein said lever is selectively coupled in hinged manner to a selected one of said connection points in order to adjust said amplitude.

7. A device according to claim 1, wherein the two liquid capacities communicate respectively with the two chambers of a two-rod actuator.

8. A device according to claim 1, wherein said two gas capacities communicate with each other and with a common rigid intermediate capacity.

9. A device according to claim 8, wherein a duct is connected between each gas capacity and said rigid intermediate capacity.

10. A device according to claim 8, wherein said rigid intermediate capacity includes said liquid detector.

11. A device according to claim 10, wherein said liquid detector is operationally connected to a system for stopping the device and/or for causing a counter of deformation cycles to stop.

12. A device according to claim 1, including a plurality of pairs of said rigid chambers receiving said separators, and wherein the corresponding gas capacities in each pair communicate with one another.

13. A device according to claim 12, wherein the gas capacities of each pair of rigid chambers communicate with each other via a rigid intermediate capacity associated with each of the corresponding pairs of gas capacities.

14. A device according to claim 13, wherein the rigid chambers are arranged side by side in a circle, and wherein the above-mentioned means for causing the volumes of liquid in the liquid capacities of each pair to vary in alternation and in phase opposition comprise a common actuator mechanism corresponding to a cam-forming ring, said cam being driven in rotation about an axis passing through the center of the circle around which said rigid chambers are arranged.

15. A device for testing the reliability of flexible separators for separating a liquid fluid and a gaseous fluid, wherein the device comprises two identical rigid chambers, each of said chambers being subdivided by an identical flexible separator into a liquid capacity and a gas capacity, wherein the two gas capacities communicate with each other, and wherein the two liquid capacities communicate with means for causing the volume in each of the two liquid capacities to vary in alternation, wherein each of the two liquid capacities communicates with a respective deformable capacity in the form of bags, the two said bags having the same volume and being subjected in alternation to identical varying deformation, and wherein each of said bags being subjected via a plate-forming rigid bottom to the action of a lever oscillating about an axis that is equidistant between said bags and that exerts similar compression forces on said bags in alternation.

16. A device for testing the reliability of flexible separators for separating a liquid fluid and a gaseous fluid, wherein the device comprises two identical rigid chambers, each of said chambers being subdivided by an identical flexible separator into a liquid capacity and a gas capacity, wherein the two gas capacities communicate with each other, and wherein the two liquid capacities communicate with means for causing the volume in each of the two liquid capacities to vary in alternation, wherein the two liquid capacities communicate respectively with the two chambers of a two-rod actuator.

17. A device for testing the reliability of flexible separators for separating a liquid fluid and a gaseous fluid, wherein the device comprises two identical rigid chambers, each of said chambers being subdivided by an identical flexible separator into a liquid capacity and a gas capacity, wherein the two gas capacities communicate with each other, and wherein the two liquid capacities communicate with means for causing the volume in each of the two liquid capacities to vary in alternation, wherein the device includes a plurality of pairs of said rigid chambers receiving said separators, wherein the corresponding gas capacities in each pair communicate with one another, wherein the rigid chambers are arranged side by side in a circle, and wherein the above-mentioned means for causing the volumes of liquid in the liquid capacities of each pair to vary in alternation and in phase opposition comprise a common actuator mechanism corresponding to a cam-forming ring, said cam being driven in rotation about an axis passing through the center of the circle around which said rigid chambers are arranged.

* * * * *